United States Patent [19]

Nakayama et al.

[11] Patent Number: 5,712,405
[45] Date of Patent: Jan. 27, 1998

[54] PREPARATION OF SILANES

[75] Inventors: Hiroshi Nakayama; Hiroshi Tsumura, both of Annaka; Tetsuo Nakanishi, Usui-gun; Yukinori Satoh, Annaka, all of Japan

[73] Assignee: Shin-Etsu Chemical Co., Ltd., Tokyo, Japan

[21] Appl. No.: 781,207

[22] Filed: Jan. 10, 1997

[30] Foreign Application Priority Data

Jan. 12, 1996 [JP] Japan .................... 8-022111

[51] Int. Cl.$^6$ .................................................. C07F 7/16
[52] U.S. Cl. ........................... 556/472; 423/341; 423/342
[58] Field of Search ......................... 556/472; 423/341, 423/342

[56] References Cited

U.S. PATENT DOCUMENTS

| | | | |
|---|---|---|---|
| 5,015,751 | 5/1991 | Feldner et al. | 556/472 |
| 5,063,040 | 11/1991 | Ruff | 423/342 |
| 5,312,948 | 5/1994 | Freeburne et al. | 556/472 |

*Primary Examiner*—Paul F. Shaver
*Attorney, Agent, or Firm*—Millen, White, Zelano & Branigan, P.C.

[57] ABSTRACT

An (alkylhalo)silane is prepared by using a fluidized bed reactor equipped with a feed line for reactant gas and a delivery line for product gas, charging the reactor with a contact mass comprising metallic silicon powder and a copper catalyst, and feeding a reactant gas containing an alkyl halide through the feed line into the reactor whereby the silane is formed by direct synthesis. A dust collector is connected to the delivery line for collecting the contact mass carried over with the product gas, which is fed back to the reactor. The feed of the reactant gas is controlled such that a linear velocity multiplied by a density may range from 0.2–2 kg/m$^2$·sec.

13 Claims, 2 Drawing Sheets

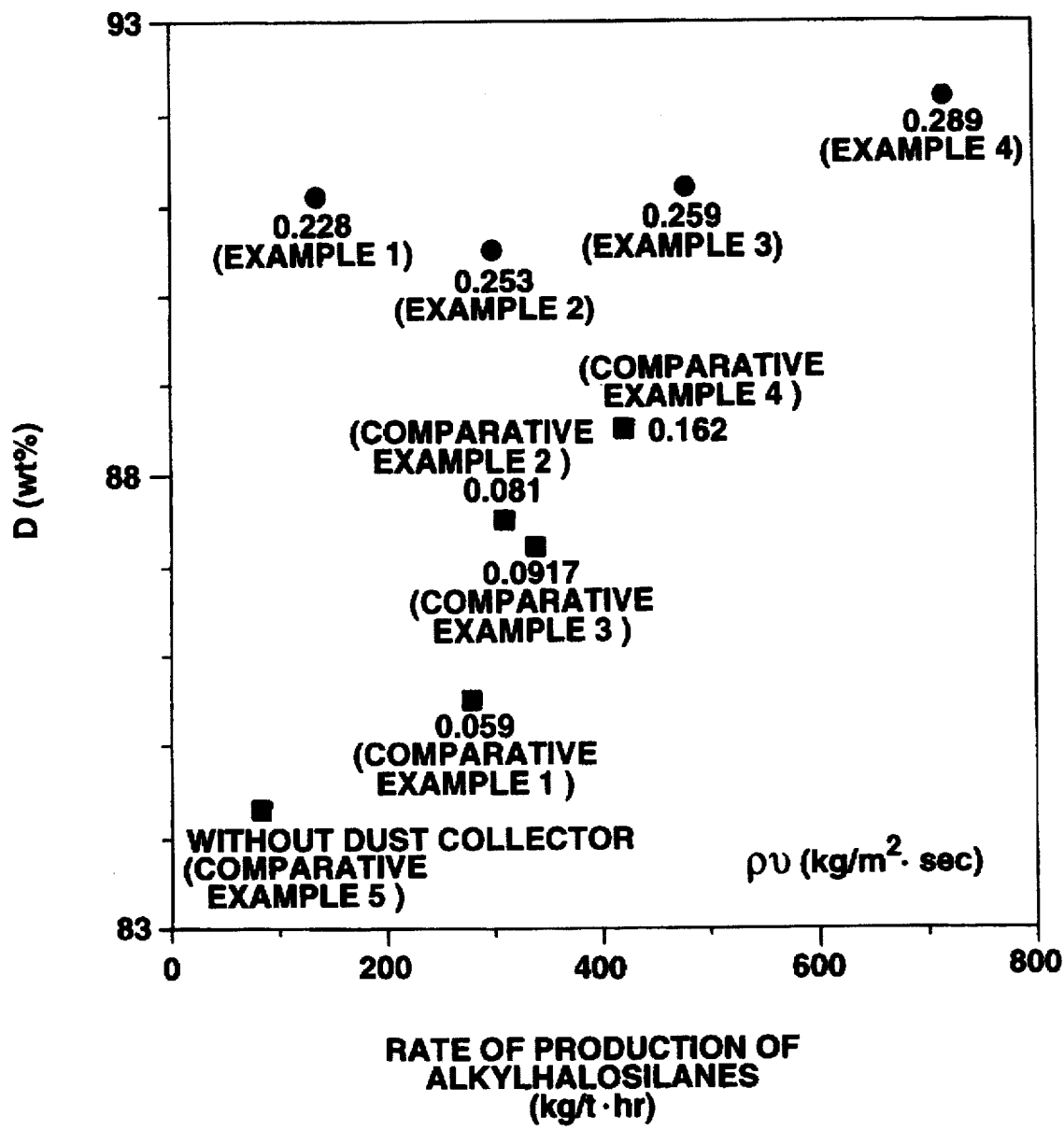

PREPARATION OF SILANES

BACKGROUND OF THE INVENTION

1. Field of the Invention

This invention relates to an improvement in the direct process for preparing (alkylhalo)silanes from metallic silicon and alkyl halides, the process being capable of forming a end product of quality at a high production rate and high selectivity in high yields.

2. Prior Art

With respect to the synthesis of alkylhalosilanes, Rochow first disclosed in U.S. Pat. No. 2,380,995 direct synthesis reaction between metallic silicon and an alkyl halide in the presence of a copper catalyst. Since then, there have been reported a number of research works relating to various co-catalysts used in the presence of copper catalyst, various copper catalysts and treatment thereof, metallic silicon, reactors, and the like.

The direct synthesis process involves activating a contact mass comprising metallic silicon, a copper catalyst, and a co-catalyst and introducing an alkyl halide into the activated contact mass for accomplishing gas-solid direct contact between the metallic silicon and the alkyl halide, thereby producing alkylhalosilanes. The industry commonly uses fluidized bed reactors for the synthesis of alkylhalosilanes.

Commercially most important among alkylhalosilanes produced by the direct synthesis process are dialkyldihalosilanes because they find a number of applications as a raw material for the production of silicone polymers. In fact, dialkyldihalosilanes have been most widely used. To increase the productivity of dialkyldihalosilane, both the rate of production of alkylhalosilanes and the selectivity of dialkyldihalosilane must be increased.

However, since the reaction of producing alkylhalosilanes is exothermic, hot spots are locally developed in the reactor as the rate of production increases. Such hot spots cause many troubles such as sintering and segregation of catalyst particles in the contact mass, deactivation of the catalyst, decomposition of alkyl halide and alkylhalosilanes, and accumulation of impurity carbon, giving rise to such problems as low selectivity and low yield. In order to maintain the selectivity of dialkyldihalosilane and continue reaction, the process must be run at a slow rate of production.

In connection with the direct synthesis of alkylhalosilanes, JP-B 40035/1989 discloses that the amount of alkyl halide fed may be at least equal to a flow rate necessary to fluidize a bed of contact mass in the reactor. Similarly, JP-A 66439/1989 also describes that the amount of alkyl halide fed may be at least equal to a gas amount necessary to fluidize a contact mass in the reactor. At a low flow velocity only sufficient to fluidize the contact mass in the reactor, however, insufficient heat transfer takes place between gas and solid, leading to aggravation of selectivity and lowering of yield. It is then difficult to continuously run the reaction.

JP-A 8219/1976 discloses that adjustment of the amount of alkyl halide-containing reactant gas fed into the reactor to a superficial linear velocity through column of 20 to 80 cm/sec. prohibits agglomeration and deposition to the reactor wall and/or distributor of reacting contact mass, avoids local heating, and improves the selectivity of dialkyldihalosilane. At an increased flow velocity, however, fines exceed the terminal velocity, are scattered and carried over along with the product gas, and eventually discharged out of the reactor system. Since such fines have a larger surface area contributing to reaction, the effective surface area participating in reaction is reduced as a result of fines exiting from the reactor system. In addition, fine particles having a smaller particle size serve to make the in-reactor temperature more uniform since better heat transfer occurs between fine particles. The discharge of fines, therefore, invites a distribution of temperature within the reactor, resulting in a lower rate of reaction, poor selectivity and lower yield.

Therefore, there is a desire to have an efficient process for preparing alkylhalosilanes.

SUMMARY OF THE INVENTION

An object of the present invention is to provide a process for preparing an (alkylhalo)silane of quality at a high rate of formation and high selectivity in a high yield.

The present invention is directed to the preparation of (alkylhalo)silanes by using a fluidized bed reactor equipped with a feed line for reactant gas and a delivery line for product gas, charging the reactor with a contact mass comprising metallic silicon powder and a copper catalyst, and feeding a reactant gas containing an alkyl halide through the feed line into the reactor whereby the (alkylhalo)silanes are formed by direct synthesis. By connecting a dust collector to the delivery line for collecting the contact mass, feeding the collected contact mass back to the reactor, and controlling the reactant gas such that a linear velocity multiplied by a density may range from 0.2 to 2 $kg/m^2 \cdot sec$, (alkylhalo)silanes, typically dialkyldihalosilane, of quality are obtained at a high rate of production and a high selectivity and in a high yield. Selective production of dialkyldihalosilane is ensured.

Accordingly, the present invention provides a process for preparing a silane using a fluidized bed reactor equipped with a feed line for reactant gas and a delivery line for product gas, comprising the steps of charging the fluidized bed reactor with a contact mass comprising metallic silicon powder and a copper catalyst, feeding a reactant gas containing an alkyl halide through the feed line into the reactor at a linear velocity and a density such that the linear velocity multiplied by the density may range from 0.2 to 2 $kg/m^2 \cdot sec$ whereby the silane is formed by direct synthesis, delivering the product gas out of the reactor through the delivery line, some of the contact mass being carried over along with the product gas, collecting the contact mass by means of a dust collector connected to the delivery line, and feeding the collected contact mass back to the reactor.

BRIEF DESCRIPTION OF THE DRAWINGS

These and further features of the present invention will be apparent with reference to the following description and drawings, wherein:

FIG. 2 is a graph showing a rate of production of alkylhalosilane vs. a percent of dialkyldihalosilane in alkylhalosilanes produced (D).

DESCRIPTION OF THE PREFERRED EMBODIMENT

Figure 1:
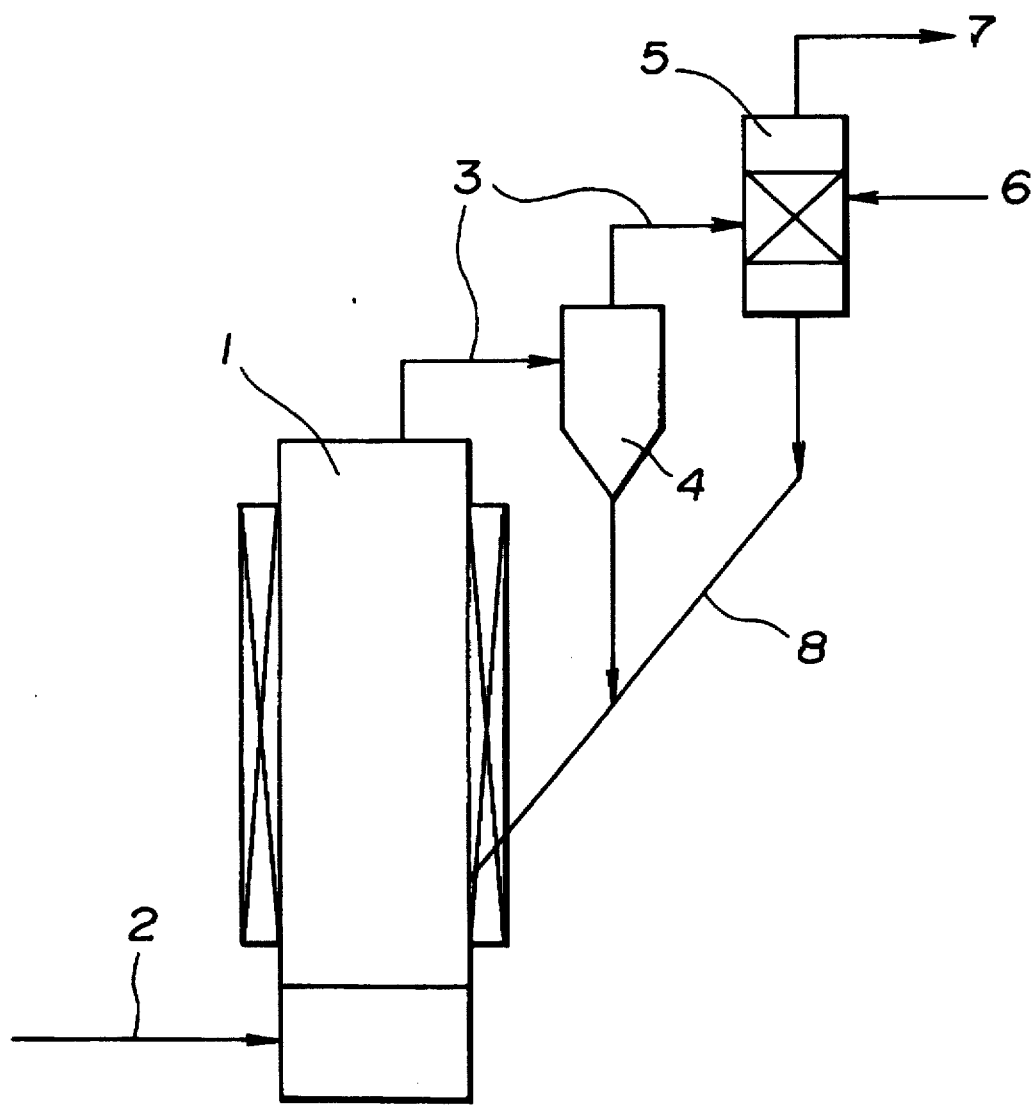
FIG. 1 is a schematic illustration of a reaction system used in the practice of the process according to the invention.

Briefly stated, the process of the present invention is to prepare (alkylhalo)silanes through direct synthesis from metallic silicon powder and an alkyl halide in the presence of a copper catalyst using a fluidized bed reactor equipped with a feed line for reactant gas and a delivery line for product gas. After the reactor is charged with a contact mass comprising metallic silicon powder and a copper catalyst, a reactant gas containing an alkyl halide is fed through the feed line into the reactor. According to the invention, a dust collector is connected to the delivery line for collecting the carried over contact mass, which is fed back to the reactor, and the supply of the reactant gas is controlled in a specific range.

The metallic silicon powder used herein is preferably particulate silicon with a purity of at least 97% by weight, especially at least 98% by weight. The metallic silicon powder should preferably have a mean particle size of 10 to 500 µm, especially 20 to 150 µm.

For the copper catalyst, any form of copper may be used, for example, elemental copper such as particulate copper powder and flake copper, copper alloys such as Cu—Zn, Cu—Si, and Cu—Sb, and copper compounds such as cuprous oxide, cupric oxide, and copper halides. The copper catalyst is preferably used in an amount of about 1 to 10 parts, especially about 2 to 8 parts by weight of copper per 100 parts by weight of the metallic silicon powder.

As is well known in the art, a promoter such as zinc, antimony and tin may be used along with the copper catalyst. The promoter may be added in a conventional amount. Zinc may be added in an amount of 0.05 to 1% by weight for the weight of the metallic silicon powder. Antimony and tin may be added in an amount of 0.01 to 0.1% by weight for the weight of the metallic silicon powder.

Alkyl halides are reacted with metallic silicon to form (alkylhalo)silanes. Exemplary alkyl halides include methyl chloride, ethyl chloride, methyl bromide, and ethyl bromide. Among these, methyl chloride is commercially most useful. Dimethyldichlorosilane prepared using methyl chloride finds numerous applications as a raw material for a variety of silicone polymers.

Desirably the alkyl halide reactant is previously heated and gasified before it is fed into the reactor. The alkyl halide gas may be used alone or in admixture with an inert gas. The inert gas used herein includes helium, argon and nitrogen.

According to the invention, an (alkylhalo)silane of the general formula (I):

$$R_nSiX_{4-n} \quad (I)$$

wherein R is a lower alkyl group having 1 to 4 carbon atoms, X is a halogen atom, and letter n is an integer of 0 to 4 is prepared from the above-mentioned reactants by direct synthesis. In formula (I), R is a lower alkyl group having 1 to 4 carbon atoms, for example, methyl, ethyl, propyl and butyl groups. X is a halogen atom, for example, chloro, bromo and fluoro.

The reactor system used in the practice of the inventive process includes a fluidized bed reactor equipped with a feed line for reactant gas and a delivery line for product gas, a dust collector disposed in the delivery line, and a feedback line extending from the collector to the reactor for feeding the collected contact mass back to the reactor. Fines which are scattered by the gas feed and carried over along with the product gas are caught by the dust collector and circulated back to the reactor through a dip leg. As a result, (alkylhalo)silanes are produced in an efficient manner.

Referring to FIG. 1, there is illustrated one preferred reactor system. The reactor system includes a fluidized bed reactor 1 surrounded by a heating jacket, a feed line 2 connected to the bottom of the reactor 1 for feeding a reactant gas, and a delivery line 3 connected to the top of the reactor 1 for delivering a product gas. A cyclone 4 and a filter unit 5 constructing a dust collector are disposed in the delivery line 3. The filter unit 5 has connected thereto a cleaning line 6 for feeding cleaning gas for cleaning the filter and an output line 7 for discharging the product gas. A feedback line 8 extends from the bottom of the filter unit 5 and cyclone 4 to the reactor 1 for feeding the collected contact mass back to the reactor 1.

The dust collector used herein should preferably be as efficient as possible, typically have a capacity to achieve a dust collection efficiency of 98% or higher. Cyclones are typical of such efficient dust collectors. Where a cyclone is used as the dust collector, it is advantageous to locate a filter such as a sintered metal filter downstream of the cyclone because disadvantages such as losses of metallic silicon by discharging of fines out of the system are mitigated.

According to the process of the invention, (alkylhalo) silanes are prepared in the reactor system as illustrated above, for example, by charging the fluidized bed reactor 1 with a contact mass comprising metallic silicon powder and a copper catalyst and introducing an inert gas into the reactor 1 through the feed line 2 to start fluidization of the contact mass. The reactor 1 is then heated to heat the contact mass to a predetermined temperature and fluidization of the contact mass is continued for a certain time for imparting catalytic activity to the contact mass. Thereafter, an alkyl halide is fed through the feed line 2 into the reactor 1 where gas-solid catalytic reaction takes place to form (alkylhalo) silanes. The product gas is discharged from the reactor 1 through the delivery line 3, passed through the cyclone 4 and filter 5, and finally delivered outside through the output line 7. While fines in the contact mass are scattered by the gas feed and carried over along with the product gas, such fines are caught by the cyclone 4 and filter 5 and fed back to the reactor 1 through the feedback line 8 by way of a dip leg.

According to the invention, the reactant gas containing an alkyl halide must be fed through the feed line 2 into the reactor 1 at a linear velocity ρ and a density υ such that the linear velocity multiplied by the density, that is, ρυ may range from 0.2 to 2 kg/m²·sec, especially 0.25 to 1.5 kg/m²·sec. With ρυ<0.2 kg/m²·sec, selectivity cannot be increased while keeping a high rate of production. With ρυ>2 kg/m²·sec, there occur implemental disadvantages, for example, the compressor used for compressing the reactant gas must be of a greater capacity and the dust collector be of a greater capacity. The density of feed gas can be controlled in terms of gas composition, temperature, and pressure. Since the reaction temperature in the direct synthesis of alkylhalosilanes preferably ranges from 250° C. to 350° C. as is well known in the art, it is preferred to control the feed gas density by adjusting the pressure while keeping the temperature within this range.

While ρυ falls within the above-defined range, the feed gas linear velocity ρ is preferably in the range of 0.05 to 1.5 m/sec., especially 0.1 to 0.8 m/sec. and the feed gas density υ is preferably in the range of 1.1 to 11 kg/m³, especially 1.6 to 5.4 kg/m³.

In the practice of the invention, it is desirable to control the concentration of alkyl halide in the feed gas such that the reaction rate may fall in the range of 50 to 1,000 kg/t·hr. A reaction rate of less than 50 kg/t·hr would be less efficient in productivity whereas a reaction rate of more than 1,000 kg/t·hr would sometimes result in low selectivity of dialkyldihalosilane due to decomposition of alkyl halide.

According to the process of the invention, (alkylhalo) silanes, typically dialkyldihalosilanes of quality are produced at a high rate of production and high selectivity in high yields.

EXAMPLE

Examples of the present invention are given below by way of illustration and not by way of limitation. All parts are by weight. In the following examples, symbols D and T have the following meaning.

D: a weight percent of dialkyldihalosilane in effective alkylhalosilanes produced T: a weight percent of alkyltrihalosilane in effective alkylhalosilanes produced T/D=(weight (kg) of alkyltrihalosilane in effective alkylhalosilanes produced)/(weight (kg) of dialkyldihalosilane in effective alkylhalosilanes produced)

Rate of production of alkylhalosilanes=(weight (kg) of effective alkylhalosilanes)/[(weight (ton) of metallic silicon)·(time (hr))]

Example 1

A reactor system with a dust collector as shown in FIG. 1 was used. The fluidized bed reactor 1 of carbon steel had a diameter of 80 mm and a height of 1,150 mm. Nitrogen gas was introduced into the reactor 1 through the feed line 2 while the reactor interior was heated to a temperature of 280° C. The reactor was charged with a contact mass, that is, 100 parts of metallic silicon powder of commercial grade having a mean particle size of 60 μm and 2.7 parts of a catalyst mixture of metallic copper, zinc and antimony powders. Nitrogen gas was introduced into the reactor 1 for fluidizing the contact mass for two hours before a gas mixture of methyl chloride and nitrogen was introduced into the reactor 1 through the feed line 2. The reaction temperature was 290° C. The product gas was discharged through the delivery line 3 while fines were carried over along with the product. The product gas was passed through the cyclone 4 and filter 5. With reaction continued, nitrogen gas was blown into the filter unit 5 through the cleaning line 6.

After the start of reaction, the reactant gas was fed at a superficial linear velocity (ρ) of 0.141 m/sec. and a density (υ) of 1.62 kg/m³. The feed gas linear velocity multiplied by feed gas density, ρυ was equal to 0.228 kg/m²·sec. By controlling the concentration of alkyl halide in the feed gas, a reaction rate of 138 kg/t·hr was maintained. Reaction was terminated when 20% by weight of the metallic silicon charge was consumed.

The product obtained when 20% by weight of the metallic silicon charge was consumed had a composition in which dimethyldichlorosilane (D) and methyltrichlorosilane (T) were 91.1% and 4.5% by weight, respectively, based on the effective methylchlorosilanes produced. T/D=0.0494.

Example 2

After reaction was started as in Example 1, the reactant gas was fed at a superficial linear velocity (ρ) of 0.07 m/sec. and a density (υ) of 3.61 kg/m³ (ρυ=0.253 kg/m²·sec.). By controlling the concentration of alkyl halide in the feed gas, a reaction rate of 300 kg/t·hr was maintained. Reaction was terminated when 20% by weight of the metallic silicon charge was consumed.

The product obtained when 20% by weight of the metallic silicon charge was consumed had a composition in which dimethyldichlorosilane (D) and methyltrichlorosilane (T) were 90.5% and 4.8% by weight, respectively, based on the effective methylchlorosilanes produced. T/D=0.0530.

Example 3

After reaction was started as in Example 1, the reactant gas was fed at a superficial linear velocity (ρ) of 0.135 m/sec. and a density (υ) of 1.92 kg/m³ (ρυ=0.259 kg/m²·sec.). By controlling the concentration of alkyl halide in the feed gas, a reaction rate of 480 kg/t·hr was maintained. Reaction was terminated when 20% by weight of the metallic silicon charge was consumed.

The product obtained when 20% by weight of the metallic silicon charge was consumed had a composition in which dimethyldichlorosilane (D) and methyltrichlorosilane (T) were 91.2% and 4.4% by weight, respectively, based on the effective methylchlorosilanes produced. T/D=0.0482.

Example 4

After reaction was started as in Example 1, the reactant gas was fed at a superficial linear velocity (ρ) of 0.135 m/sec. and a density (υ) of 2.14 kg/m³ (ρυ=0.289 kg/m²·sec.). By controlling the concentration of alkyl halide in the feed gas, a reaction rate of 720 kg/t·hr was maintained. Reaction was terminated when 20% by weight of the metallic silicon charge was consumed.

The product obtained when 20% by weight of the metallic silicon charge was consumed had a composition in which dimethyldichlorosilane (D) and methyltrichlorosilane (T) were 92.2% and 3.8% by weight, respectively, based on the effective methylchlorosilanes produced. T/D=0.0412.

Comparative Example 1

After reaction was started as in Example 1, the reactant gas was fed at a superficial linear velocity (ρ) of 0.045 m/sec. and a density (υ) of 1.31 kg/m³ (ρυ=0.059 kg/m²·sec.). By controlling the concentration of alkyl halide in the feed gas, a reaction rate of 278 kg/t·hr was maintained. Reaction was terminated when 20% by weight of the metallic silicon charge was consumed.

The product obtained when 20% by weight of the metallic silicon charge was consumed had a composition in which dimethyldichlorosilane (D) and methyltrichlorosilane (T) were 85.5% and 8.2% by weight, respectively, based on the effective methylchlorosilanes produced. T/D=0.0960.

Comparative Example 2

After reaction was started as in Example 1, the reactant gas was fed at a superficial linear velocity (ρ) of 0.045 m/sec. and a density (υ) of 1.80 kg/m³ (ρυ=0.081 kg/m²·sec.). By controlling the concentration of alkyl halide in the feed gas, a reaction rate of 308 kg/t·hr was maintained. Reaction was terminated when 20% by weight of the metallic silicon charge was consumed.

The product obtained when 20% by weight of the metallic silicon charge was consumed had a composition in which dimethyldichlorosilane (D) and methyltrichlorosilane (T) were 87.5% and 6.9% by weight, respectively, based on the effective methylchlorosilanes produced. T/D=0.0789.

Comparative Example 3

After reaction was started as in Example 1, the reactant gas was fed at a superficial linear velocity (ρ) of 0.07 m/sec. and a density (υ) of 1.31 kg/m³ (ρυ=0.092 kg/m²·sec.). By controlling the concentration of alkyl halide in the feed gas, a reaction rate of 338 kg/t·hr was maintained. Reaction was terminated when 20% by weight of the metallic silicon charge was consumed.

The product obtained when 20% by weight of the metallic silicon charge was consumed had a composition in which dimethyldichlorosilane (D) and methyltrichlorosilane (T)

were 87.2% and 6.8% by weight, respectively, based on the effective methylchlorosilane produced. T/D=0.0780.

Comparative Example 4

After reaction was started as in Example 1, the reactant gas was fed at a superficial linear velocity (ρ) of 0.135 m/sec. and a density (υ) of 1.20 kg/m³ (ρυ=0.162 kg/m²·sec.). By controlling the concentration of alkyl halide in the feed gas, a reaction rate of 420 kg/t·hr was maintained. Reaction was terminated when 20% by weight of the metallic silicon charge was consumed.

The product obtained when 20% by weight of the metallic silicon charge was consumed had a composition in which dimethyldichlorosilane (D) and methyltrichlorosilane (T) were 88.5% and 6.3% by weight, respectively, based on the effective methylchlorosilanes produced. T/D=0.0712.

Comparative Example 5

After reaction was started as in Example 1 except that the dust collector was removed from the reactor, the reactant gas was fed at a superficial linear velocity (ρ) of 0.135 m/sec. and a density (υ) of 1.91 kg/m³ (ρυ=0.258 kg/m²·sec.). Although the concentration of alkyl halide in the feed gas was controlled, the reaction rate reached only 84 kg/t·hr. Reaction was terminated when 20% by weight of the metallic silicon charge was consumed.

The product obtained when 20% by weight of the metallic silicon charge was consumed had a composition in which dimethyldichlorosilane (D) and methyltrichlorosilane (T) were 84.3% and 9.5% by weight, respectively, based on the effective methylchlorosilanes produced. T/D=0.113.

The results of Examples and Comparative Examples are shown in Table 1.

TABLE 1

|  | E1 | E2 | E3 | E4 | CE1 | CE2 | CE3 | CE4 | CE5 |
| --- | --- | --- | --- | --- | --- | --- | --- | --- | --- |
| Feed gas density υ (kg/m³) | 1.62 | 3.61 | 1.92 | 2.14 | 1.31 | 1.80 | 1.31 | 1.20 | 1.91 |
| Feed gas linear velocity ρ (m/sec) | 0.141 | 0.07 | 0.135 | 0.135 | 0.045 | 0.045 | 0.07 | 0.135 | 0.135 |
| ρυ (kg/m² · sec) | 0.228 | 0.253 | 0.259 | 0.289 | 0.059 | 0.081 | 0.0917 | 0.162 | 0.258 |
| Dust collector | YES | YES | YES | YES | YES | YES | YES | YES | NO |
| Rate of production of alkylhalosilane (kg/t · hr) | 138 | 300 | 480 | 720 | 278 | 308 | 338 | 420 | 84 |
| D (wt %) | 91.1 | 90.5 | 91.2 | 92.2 | 85.5 | 87.5 | 87.2 | 88.5 | 84.3 |
| T (wt %) | 4.5 | 4.8 | 4.4 | 3.8 | 8.2 | 6.9 | 6.8 | 6.3 | 9.5 |
| T/D | 0.0494 | 0.053 | 0.0482 | 0.0412 | 0.0960 | 0.0789 | 0.0780 | 0.0712 | 0.113 |

The results are also plotted in the graph of FIG. 2 wherein D is on the ordinate and the rate of production of alkylhalosines is on the abscissa.

It is evident from Table 1 and FIG. 2 that reactivity is significantly improved by attaching a dust collector to a reactor and feeding collected fines back to the reactor. By controlling ρυ so as to fall within the specific range, dimethyldichlorosilane is produced at a high rate of reaction and high selectivity.

Although some preferred embodiments have been described, many modifications and variations may be made thereto in the light of the above teachings. It is therefore to be understood that within the scope of the appended claims, the invention may be practiced otherwise than as specifically described.

We claim:

1. A process for preparing a silane of the general formula $$R_n SiX_{4-n} \tag{I}$$

wherein R is a lower alkyl group having 1 to 4 carbon atoms, X is a halogen atom, and letter n is an integer of 0 to 4, using a fluidized bed reactor equipped with a feed line for reactant gas and a delivery line for product gas, comprising the steps of charging the fluidized bed reactor with a contact mass comprising metallic silicon powder and a copper catalyst, feeding a reactant gas containing an alkyl halide through the feed line into the reactor at a linear velocity and a density such that the linear velocity multiplied by the density ranges from 0.2 to 2 kg/m²·sec whereby the silane is formed by direct synthesis, delivering the product gas out of the reactor through the delivery line, some of the contact mass being carried over along with the product gas, collecting the contact mass by means of a dust collector connected to the delivery line, and feeding the collected contact mass back to the reactor.

2. The method of claim 1, wherein the metallic silicon powder is particulate silicon with a purity of at least 97% by weight.

3. The method of claim 1, wherein the metallic silicon powder has a mean particle size of 10 to 500 μm.

4. The method of claim 1, wherein the metallic silicon powder has a mean particle size of 20 to 150 μm.

5. The method of claim 1, wherein the copper catalyst is particulate copper powder, flake copper, Cu—Zn alloy, Cu—Si alloy, Cu—Sb alloy, cuprous oxide, cuptic oxide or a copper halide.

6. The method of claim 1, wherein the copper catalyst is used in an amount of about 1 to 10 parts by weight of copper per 100 parts by weight of the metallic silicon powder.

7. The method of claim 1, wherein a zinc, antimony or tin promoter is used together with the copper catalyst.

8. The method of claim 1, wherein the alkyl halide is methyl chloride, ethyl chloride, methyl bromide or ethyl bromide.

9. The method of claim 1, further comprising heating and gasifying the alkyl halide before it is fed into the reactor.

10. The method of claim 1, wherein the reactant gas further comprises an inert gas.

11. The method of claim 1, wherein the reactant gas linear velocity multiplied by the density is from 0.25 to 0.15 kg/m²·sec.

12. The method of claim 1, wherein the reaction temperature is from 250° C. to 350° C.

13. The method of claim 1, wherein the linear velocity of the reactant gas is from 0.5 to 1.5 m/sec and the reactant gas density is from 1.1 to 11 kg/m³.

* * * * *